United States Patent
De Gaulle et al.

(10) Patent No.: US 7,575,936 B2
(45) Date of Patent: Aug. 18, 2009

(54) METHOD FOR MAKING ENHANCING THE RELIABILITY OF THE TRACEABILITY OF BLOOD SAMPLES

(75) Inventors: Antoine De Gaulle, Paris (FR); Jean-Claude Mongrenier, Saint Germain en Laye (FR)

(73) Assignee: Biolog, Boulogne Billancourt (FR)

( * ) Notice: Subject to any disclaimer, the term of this patent is extended or adjusted under 35 U.S.C. 154(b) by 869 days.

(21) Appl. No.: 10/482,408

(22) PCT Filed: Jul. 12, 2002

(86) PCT No.: PCT/FR02/02465

§ 371 (c)(1),
(2), (4) Date: Apr. 1, 2004

(87) PCT Pub. No.: WO13/011364

PCT Pub. Date: Feb. 13, 2003

(65) Prior Publication Data
US 2004/0151633 A1   Aug. 5, 2004

(30) Foreign Application Priority Data
Jul. 12, 2001   (FR) .................. 01 09246

(51) Int. Cl.
*G01N 1/00* (2006.01)

(52) U.S. Cl. .................... 436/174

(58) Field of Classification Search .......... 436/174; 604/408
See application file for complete search history.

(56) References Cited

U.S. PATENT DOCUMENTS

| | | | | |
|---|---|---|---|---|
| 4,985,153 A | * | 1/1991 | Kuroda et al. | 210/782 |
| 5,100,564 A | * | 3/1992 | Pall et al. | 210/782 |
| 5,674,741 A | * | 10/1997 | Watanabe et al. | 435/283.1 |
| 5,980,501 A | * | 11/1999 | Gray | 604/408 |
| 6,113,554 A | | 9/2000 | Gilcher et al. | |
| 6,285,285 B1 | * | 9/2001 | Mongrenier | 340/572.8 |
| 6,402,702 B1 | | 6/2002 | Gilcher et al. | |

FOREIGN PATENT DOCUMENTS

| | | |
|---|---|---|
| EP | 0639384 | 2/1994 |
| EP | 1072030 | 1/2001 |
| FR | 2796182 | 1/2001 |

* cited by examiner

*Primary Examiner*—Walter D Griffin
*Assistant Examiner*—Bobby Ramdhanie
(74) *Attorney, Agent, or Firm*—Greenblum & Bernstein, P.L.C.

(57) ABSTRACT

Method for enhancing the reliability of the traceability of blood samples resulting from collection of whole blood in a mother blood bag using sampling kits, whose contents vary depending on the blood products needed and statutory regulations, and which are mainly composed of bags connected to each other by tubes and incorporating at least one filtration unit. Each bag includes an electronic chip capable of memorising and exchanging information with an electronic communication device. This abstract is not intended to define the invention disclosed in the specification, nor intended to limit the scope of the invention in any way.

27 Claims, 4 Drawing Sheets

METHOD FOR MAKING ENHANCING THE RELIABILITY OF THE TRACEABILITY OF BLOOD SAMPLES

CROSS-REFERENCE TO RELATED APPLICATIONS

The present application is a U.S. National Stage of International Patent Application No. PCT/FR02/02465 filed Jul. 12, 2002 which published as WO 03/011364 on Feb. 13, 2003, and claims priority of French Patent Application No. 01/09246 filed Jul. 12, 2001.

BACKGROUND OF THE INVENTION

Field of the Invention

The present invention concerns a method for enhancing the reliability of the traceability of blood samples, more particularly during plasma and red blood cell collection operations.

All the blood collected from a donor is transferred into a mother blood bag, connected to the donor via a catheter pushed into a vein, itself attached by a flexible tube to the said mother blood bag placed on a weighing and stirring device which enables a given quantity of blood to be collected. The mother blood bag is connected to other bags whose configurations vary depending on the donor's characteristics, notably for extracting plasma, red blood cells and even platelets; each blood bag configuration constitutes what is hereinafter called a "sampling kit".

Numerous different sampling kits exist, that evolve depending on working habits and/or regulations; in the following text, a sampling kit is described for use in support of explanations on enhancing the reliability of the traceability of blood bags; these explanations are also valid for sampling kits other than the one described below.

For example, the said mother blood bag described above is connected by a second flexible tube to a first leukocyte filter fitted with a by-pass for short-circuiting it, should platelets need to be extracted in a subsequent operation; the first filtration unit is connected by a third flexible tube to a primary blood bag; the primary blood bag is in turn connected to a fourth flexible tube which separates into two to form a fifth flexible tube that incorporates a second filtration unit, connected to a plasma bag and a sixth flexible tube connected to an anti-coagulant bag; the fourth tube is connected to the same side of the primary blood bag as the third tube. The plasma and anti-coagulant bags contain foolproof devices, which are used when the phases are separated.

In the following text, a theoretical method for processing whole blood that has been collected is described, but only in support of explanations.

Once the whole blood has been collected in the mother blood bag, the first flexible tube is heat-sealed and the mother blood bag, after separation from the catheter is hung upright so that the first filtration unit and the primary blood bag can be hung onto the mother blood bag; the plasma and anti-coagulant bags can be hung, or not, onto the primary blood bag and the fourth tube is stopped to prevent the filtered blood from going into the plasma bag. The second and third tubes are then opened so that the blood contained in the mother blood bag can flow through the first filtering device down into the primary blood bag.

Once the blood has been filtered, the third tube is heat-sealed and the unit formed by the first filtration unit and the mother blood bag can be separated from the primary blood bag.

The primary blood bag, the plasma bag and the anti-coagulant bag are then placed in a centrifuge; this operation consists firstly in placing a primary blood bag in each of the stiff plastic, completely open centrifuge containers with the third and fourth flexible tube connections facing upwards towards the top of the container and their plasma and anticoagulant bags; then the two containers are each placed on one of the two pans on a pair of scales, for matching their weight accurately for centrifuging; each centrifuge container is placed in one of the two centrifuge bowls in the centrifugal separator; the centrifuging operation is carried out following a pre-set process, then the centrifuged containers are removed from the centrifuge bowls and the centrifuged primary blood bags and plasma and anticoagulant bags are then removed from their containers; any centrifuged primary blood bags that have leaked during this operation are eliminated; the contents of the all other centrifuged primary blood bags include two main phases, which are, on the one hand, a phase with a high red blood cell content that has accumulated in the bottom of the primary blood bag and, on the other hand, a phase composed of plasma that floats on the top; the primary and secondary blood bags are put into a separator.

The separator contains three cradles for holding the blood bags; a first cradle is designed for holding the primary blood bag, a second cradle is for the plasma bag and a third cradle for the anticoagulant bag; the first cradle is placed beneath the two other cradles; the three cradles each form an enclosed, normally parallelepiped shaped cavity with two large side faces that are composed of, on one side, a flat door covering virtually the total surface of the face and which opens up to the outside of the separator, and, on the other side, a non-fixed flat sidewall capable of moving in parallel to itself on an axis perpendicular to the plane of the main faces.

With the phase containing the high red blood cell content at the bottom, the primary blood bag is positioned vertically in the first cradle, whose mobile vertical sidewall has been pushed sufficiently far backwards for the bag to be completely inserted and the door to be closed; the plasma bag intended for holding the plasma is placed in the second cradle that notably contains a guide system for preventing the anticoagulant bag from being inserted in its place; the anticoagulant bag contains anticoagulant intended for use with the phase with the high red blood cell content; this bag is placed in the third cradle, which also contains a guide system and a mobile sidewall, which has been pushed sufficiently far backwards for the bag to be inserted; the fifth tube passes through a first closing device, located between the second filtration unit and the plasma bag, which enables the tube either to be temporarily closed by compressing it, or to be heat-sealed and cut for separating the primary blood bag from the plasma bag containing the plasma; this operation is carried out by cutting the tube in such a way that the tube is heat-sealed on both the primary blood bag side and the plasma bag side; similarly the sixth tube goes through a second closing device, which, as described above, either compresses the sixth tube to close it temporarily or permanently closes it by heat-sealing and then separates the anticoagulant bag from the primary blood bag.

On starting up the separator, after the primary blood bag, the plasma bag and the anticoagulant bag have been put in place, the second closing device compresses the sixth tube to hold it closed, whereas the fifth tube remains open from end to end; the mobile sidewall on the second cradle, driven by a pressure cylinder, comes into contact with the plasma bag, whilst the mobile sidewall in the first cradle is pushed by a pressure cylinder to compress the primary blood bag sufficiently for expelling the plasma upwards through the second filtration unit toward the plasma bag which gradually swells and pushes the second cradle's mobile sidewall backwards; an optical control device, through which the fourth tube passes, detects the arrival of the phase with the high red blood cell content, at which time a new operation is set off that consists, notably, of closing the fifth tube, heat-sealing and cutting it, followed by opening the sixth tube, which allows the contents of the anticoagulant bag to be transferred to the primary blood bag, by compressing the former and easing back the mobile sidewall on the first cradle; the sixth tube is then heat-sealed and cut so that the anticoagulant bag is separated from the primary blood bag. The phase with the high red blood cell content remains in the primary blood bag and the sixth tube is heat-sealed and cut to separate it from the anticoagulant bag that is now empty.

During these different operations, information on each operation must be added to previously obtained information, and all the information must be completely transferred several times: information on the mother blood bag must be completed by information on the filtration process, all of which information must then be transferred to the primary blood bag, because the mother blood bag and the first filtration unit are removed after the third tube has been heat-sealed and cut; specific filtration information needing to be transferred includes, for example, the identity of operators, the references of support equipment, the duration of the operation, the date on which the operation was completed (in this case the word "date" signifies date and time) and any possible incidents. The conditions under which centrifugation has been carried out are marked on the primary blood bag; they refer, for example, to the machine number, the operator's identity, centrifugation speed and duration and any possible incidents that may have occurred during the operation. Separation of the phase with the high red blood cell content from the plasma implies putting new information onto the plasma bag that comes from the primary blood bag, together with information concerning the separation operation, as well as any new information that may need to be put on the primary blood bag concerning the anticoagulant bag and the separation operation.

The large number of operations to be carried out for recopying information and the need to put new information on the blood bag concerned after each operation is a source of error liable to make it impossible to trace blood samples correctly.

A device for tracing blood samples, as per patent EP 1 072 030, is under development: it associates an electronic chip with the blood bag; every electronic chip contains a loop antenna, which communicates with a loop antenna on an electronic communication device connected to a computer system capable of supplying the electronic chip with energy, on the one hand, and, on the other, with data which it stores in memory and which it is capable of restoring to the said computer through the electronic communication device; an electronic mother chip is attached to the mother blood bag which receives all the data concerning the donor and the results of analyses for qualifying the mother blood bag; the electronic mother chip is, for example, fixed on a possibly rectangular-shaped flexible chip support several centimeters long, on which is printed a metallized loop circuit that forms the communications loop antenna; in a preferred version of the invention, the flexible chip support for the electronic mother chip is placed on one of the main surfaces of the mother blood bag beneath a rectangular label covering the major part of one of the main surfaces. The primary electronic chip equipping the primary blood bag is placed under a label that covers the main surface but in a different place when compared with the mother blood bag so that, when the mother and primary blood bags are placed one above the other, the mother and primary chips are not above each other. The same system applies for the first and second electronic chips equipping the plasma and anticoagulant bags. Preferably, chip supports are always put in the same position in relation to the label so as to make it easier to position the antenna on the electronic communication device, for recording details on the blood donor and collection conditions on the electronic mother chip on the mother blood bag.

The purpose of the invention lies in adapting equipment used in filtration, centrifugation and separation operations for enhancing the reliability of the traceability of blood samples contained in blood bags equipped with electronic chips.

DETAILED DESCRIPTION OF THE INVENTION

DETAILED DESCRIPTION OF THE INVENTION

Figure 1:
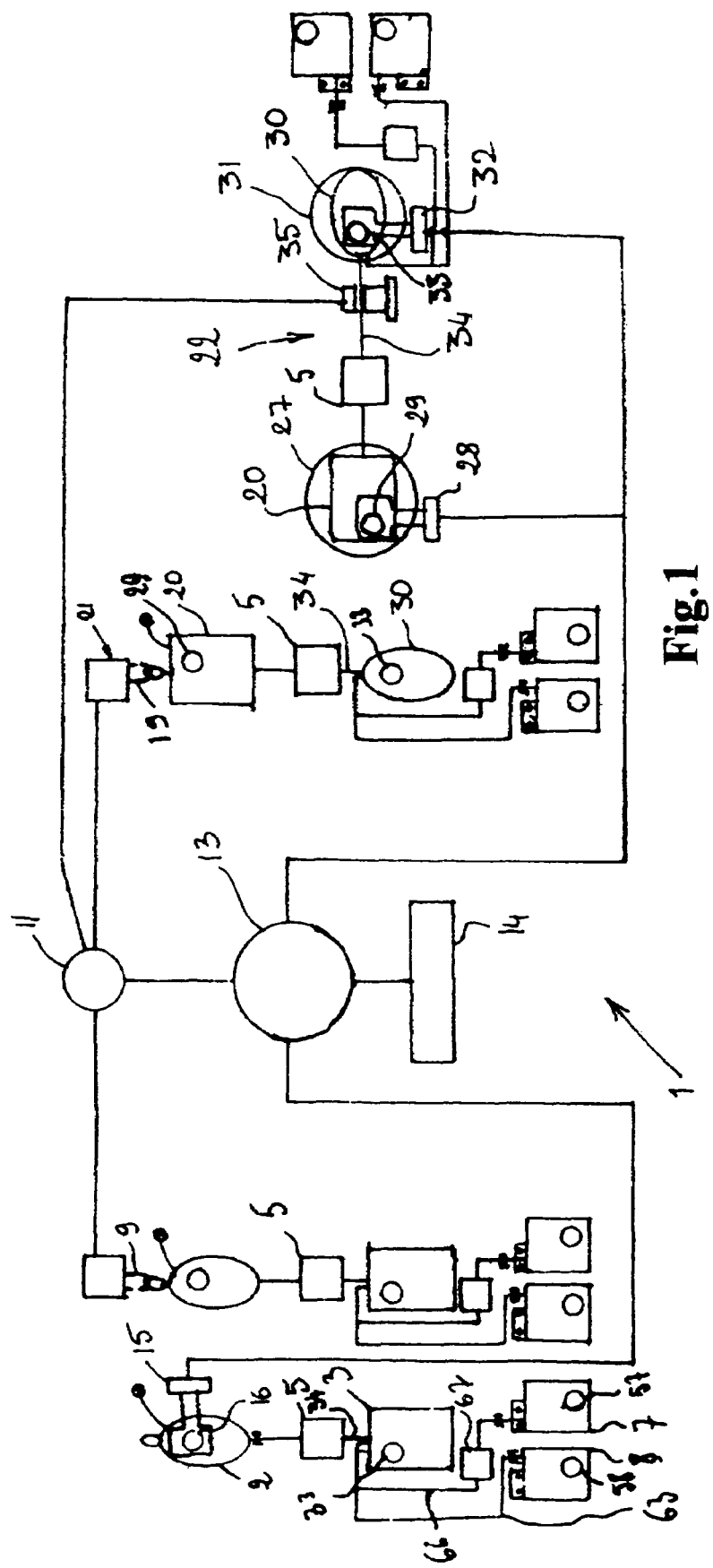
FIG. 1 represents a schematic diagram on enhancement of traceability reliability during the different filtration phases.
Figure 2:
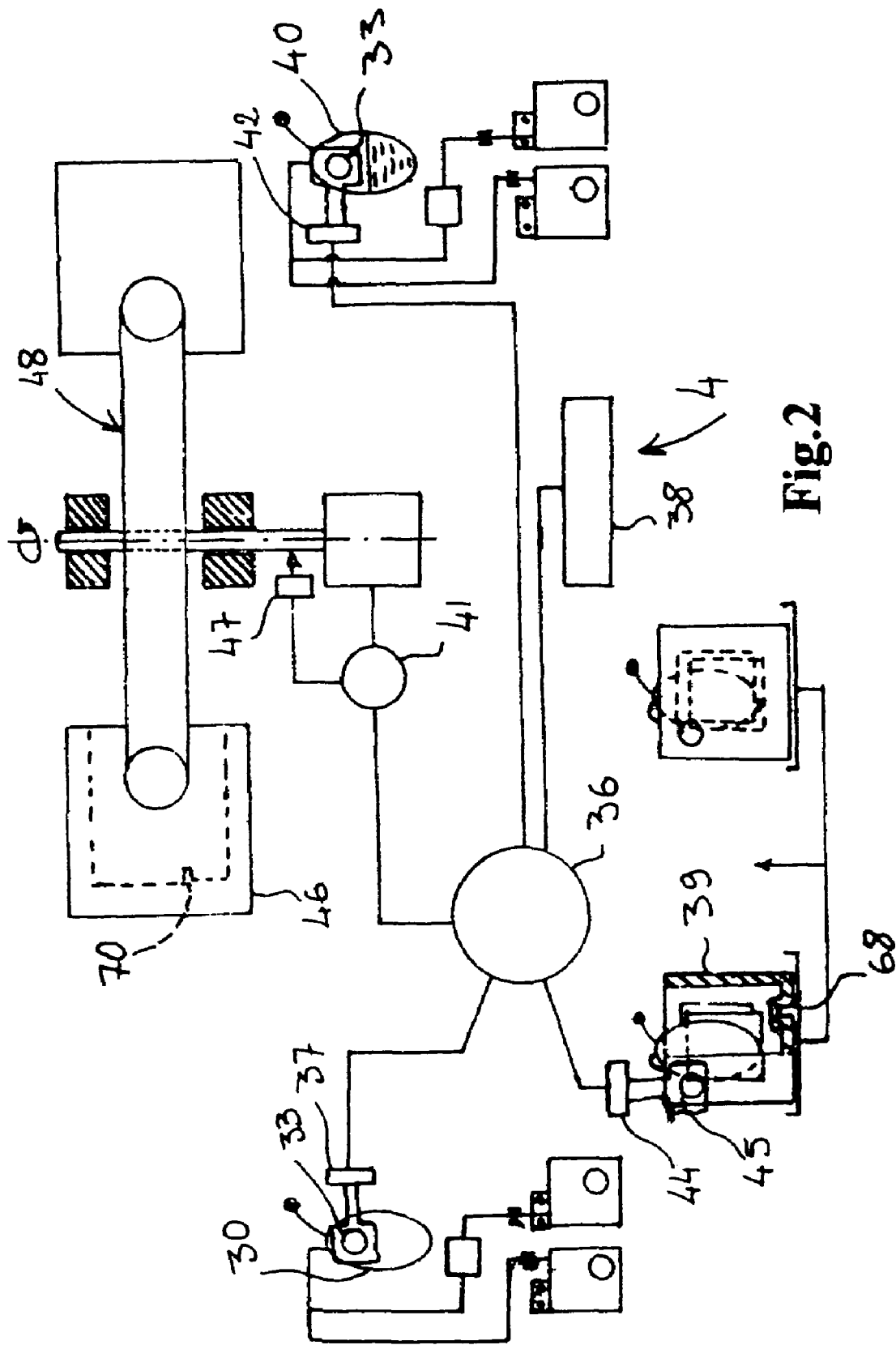
FIG. 2 represents a schematic diagram on enhancement of traceability reliability during the different centrifugation phases: an exploded view is given of a centrifuge container.
Figure 3:
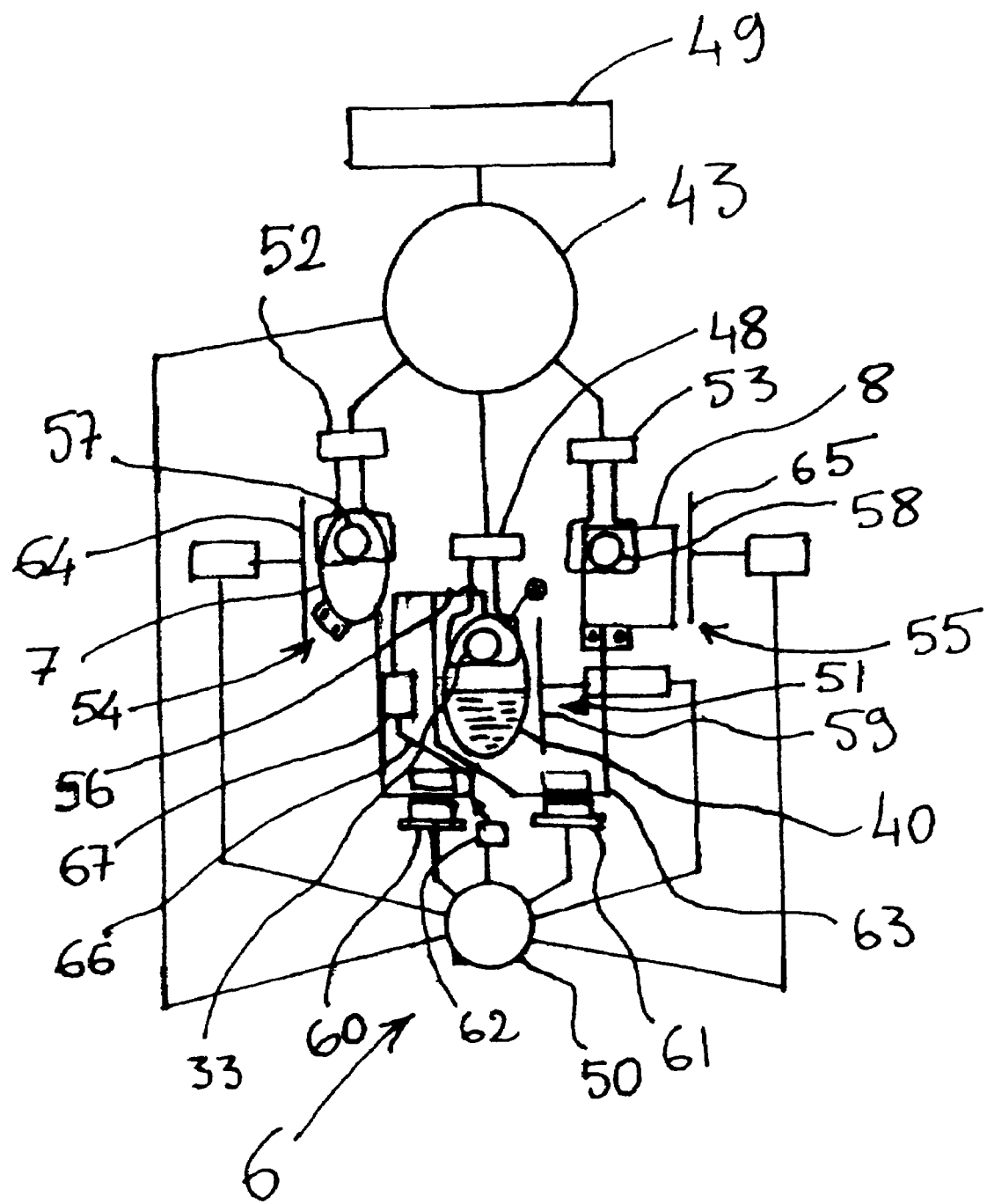
FIG. 3 represents a schematic diagram on enhancement of traceability reliability during the different centrifugation phases.

In a preferred version, the invention consists of incorporating into each filtration, centrifugation and separation machine process computerized system of collecting and processing information concerning blood sample traceability, coming from the blood bag to be processed, from the machine itself and from machine operators; these information technology resources are associated with a system of collecting information and transferring it to the blood bag(s) containing the transformed blood products, completed by methods of enhancing reliability that more particularly concern handling: at the beginning of the operation, collecting information consists of collecting information contained in the electronic chip of the blood bag to be processed and completing it with information concerning processing conditions, which are, for example, collected from the machine controller, notably, for example, the date, the number of the machine and its operating parameters, the said information also being supplied by the operator who may, for example, identify himself either via a badge or by using the keyboard. Information concerning the filtration unit 1 (FIG. 1) is transferred to the primary blood bag 3 when it is full of blood filtered through a first filtration unit 5 that has initially come from mother blood bag 2; information concerning the centrifugation device 4 (FIG. 2) is transferred to the primary centrifuged blood bag 40 which, before centrifuging, used to be the primary filtered blood bag 30: information concerning the separation device 6 (FIG. 3) coming from the primary centrifuged blood bag 40 and the anticoagulant bag 8 is transferred, on the one hand, to the plasma bag 7, after it has been filled with plasma and, on the other hand, to the primary centrifuged blood bag 40 when it only contains the phase with the high red blood cell content; information collection and transfer methods are completed by methods of enhancing reliability, that consist of, on the one hand, transmitting the information to the right consignee bag and, on the other hand, transmitting all the information required for guaranteeing correct traceability.

Figure 4A:
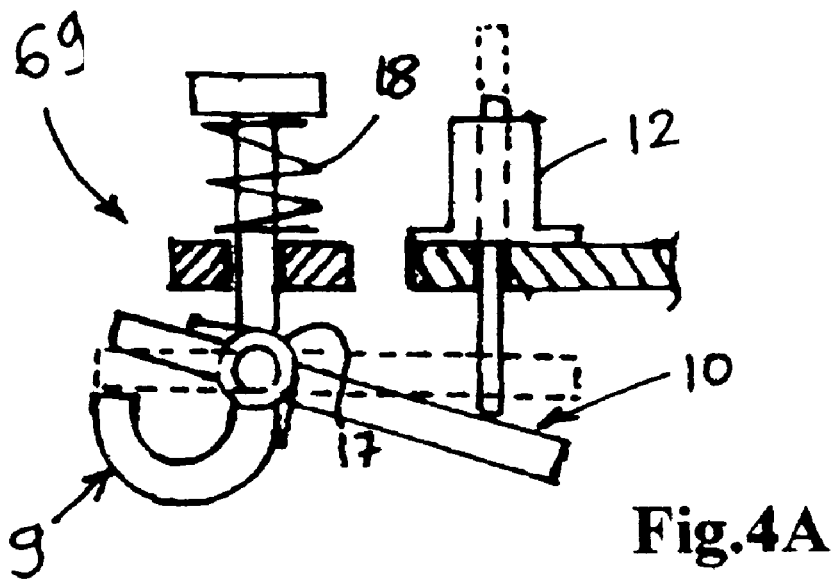
FIG. 4A represents the hook on the hanging unit used for hanging mother blood bags prior to filtration.
Figure 4B:
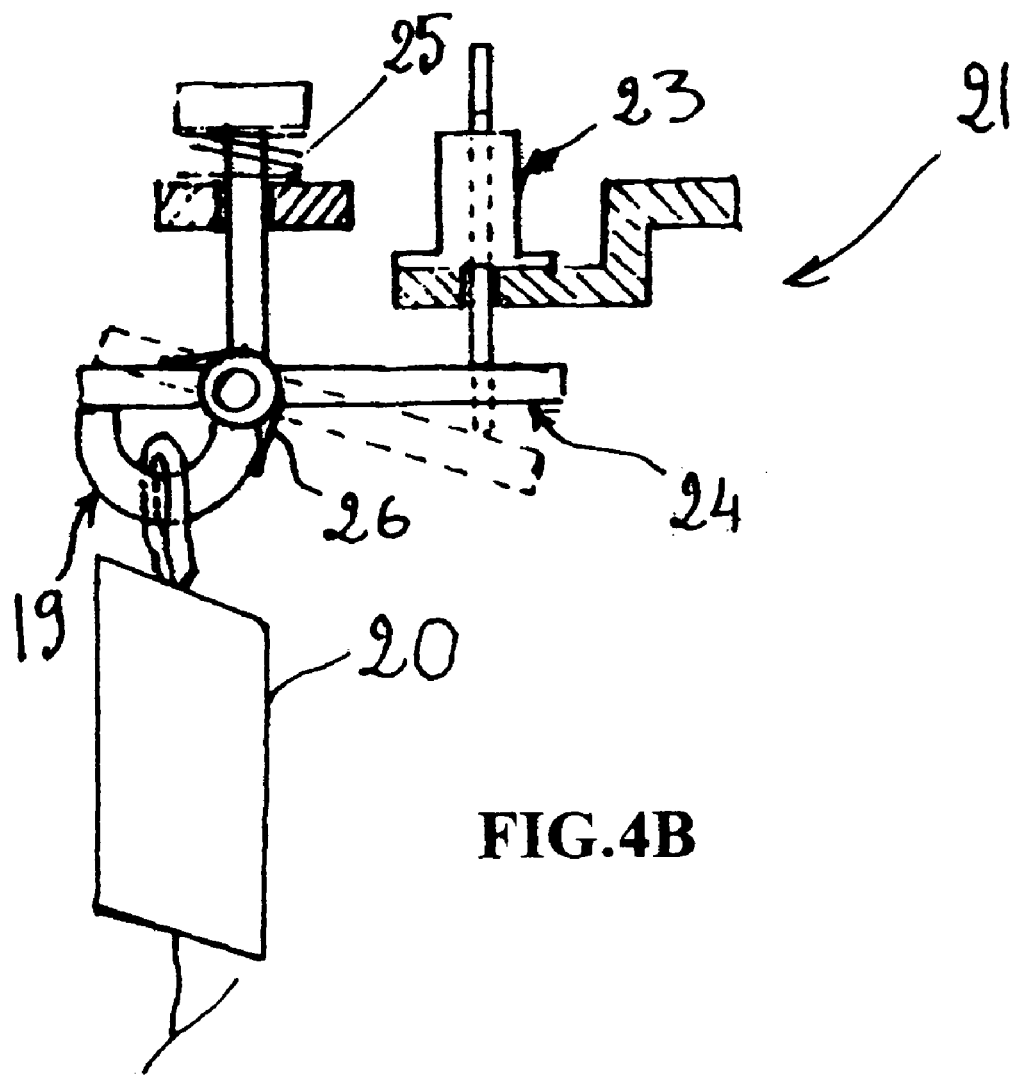
FIG. 4B shows the hook on the hanging unit in position for unloading the mother blood bag, when the bags are empty after filtration.

Concerning the filtration unit 1 (FIG. 1), one way of proceeding consists, for example, in positioning hooks 9 for the mother blood bags 2, that are incorporated in a filtration unit, programmed to command filtration operations; the number of hooks 9 is determined by the number of bags to be processed per day; the hooks 9 can be fixed or incorporated into a carousel; for example, hook 9 (FIG. 4A) is equipped with an opening-closing system 10 operated, for example, via a first electro-mechanical device 12 controlled by an electronic control system 11 (FIG. 1) incorporated into the filtration unit. When at rest, hooks 9 are closed, and a mother blood sample cannot be hung on them; the machine possesses, for example, a first computerised management device 13, especially for the filtration unit 1, controlled from a keyboard 14, through which permanent operating parameters can be entered into the filtration unit such as, for example, the date, the machine number, the conditions to be met for opening or closing hook 9, together with variable parameters such as, for example, the identity of the operator or information concerning problems of filtration: an electronic communication device 15, handled by the operator is connected to the first computerised management device 13; with the first electronic communication device 15, the operator reads the contents of the mother chip 16 on the mother bag 2, records them in the first computerised management device 13, adds the date of the beginning of the filtration process and allocates a hook 9 to the mother bag 2 concerned; the hook 9 (FIG. 4a) selected then opens, activated, for example, by the first electro-mechanical device 12 controlled in turn by the first computerised management device 13 (FIG. 1) via the electronic control device 11. When, for example, the hook 9 arrives at a loading point 69; the hook is opened by tilting the opening-closing device 10 (FIG. 4A), which puts a helical spring 17 under tension; when the operator hangs the blood bag 2 on selected hook 9 (FIG. 4A), the weight of the bag makes the hook 9 close by pulling it downwards, compressing the coil spring 18 and relieving the tension on the helix spring 17, which pulls down the opening-closing device 10; a limit switch then indicates that the mother blood bag is hooked on correctly; when the filtration operation is over, the operator, on observing that this is the case, gives the order for opening the hook concerned 19 (FIG. 4B), either by using his keyboard 14 (FIG. 1) or by a specific control system close to the hook 19, and a new date is entered in the first computerised management device 13; the hook 19 (FIG. 1 and FIG. 4B) opening at the unloading point 21, for example, by activating a second electromechanical device 23 that pushes on the opening-closing device 24 and puts the helix spring 26 under tension; the empty mother blood bag 20 is removed when it arrives at unloading station 21; it is placed on a heat-sealing and cutting apparatus 22 and the hook 19 is re-closed; it is re-closed, for example, by withdrawing the second electromechanical device 23 and releasing the tension on the helix spring 26 when at unloading station 21 and the escape and upward movement of the hook 19 due to the compressed coil spring 25 that is activated when the hook 19 leaves the unloading station 21 and rises upwards: a limit switch indicates that the mother blood bag has been unloaded, and, when it has been separated from the primary blood bag and information has been correctly transmitted to the primary blood bag, the hook 19 is then ready for re-use.

The heat-sealing and cutting device 22 (FIG. 1) includes a first heat-sealing device 35 that heat-seals the third tube 34 and separates the empty mother blood bag 20 together with its first filtration unit 5 from the primary blood bag 30 by cutting the tube in the centre of the part of the tube closed by heat-sealing; the heat-sealing and cutting apparatus 22 also contains, for example, a first compartment 27, in which the empty mother blood bag is placed; this first compartment 27 is fitted with a second electronic communication device 28 that re-reads the contents of the electronic mother chip 29 on the empty mother blood bag 20 and identifies the mother blood bag concerned 2 in the first computerised management device 13; the primary blood bag 30 is placed in a second compartment 31 fitted with a third electronic communication device 32 that records the data on this sample contained in the first computerised management device 13 onto the primary electronic chip 33; the third tube 34 is inserted in the heat-sealing and welding device 35; then, when all the information has been transmitted correctly, the computerised management device 13 gives an order to the electronic control device 11 for the first heat-sealing and cutting device 35 to carry out a heat-sealing and cutting operation with the cut made in the middle of the heat-sealed section.

Concerning the centrifuging function, the centrifuging device 4 (FIG. 2) is equipped with a second computerized management device 36 connected to a fourth electronic communication device 37 and to a keyboard 38, which is capable of receiving all information on centrifugation conditions directly. Before inserting each of the two primary blood bags 30, into one of the centrifuge containers 39, the primary electronic chips 33 are read by the fourth electronic communication device 37 and the information they contain is stored partially or completely in the second computerized management device 36. As all the information on centrifugation must be put back on the same primary blood bag 30 that has now been centrifuged and is hereafter called "the centrifuged primary blood bag 40", only information needed for identifying the primary blood bag 30 can be used. Then, the primary blood bag 30 is inserted into the centrifuge container 39 which is fitted with a container electronic chip 45, constituting a system of identification, integrated, for example, into its side-wall, and which contains identification criteria that is specific to the centrifuge container in question and into which a fifth electronic communication device 44 sends the characteristics of the primary blood bag 30 that it contains. The primary blood bag 30 should preferably be fitted with a foolproof device that enables the blood bag to be positioned so that connections for the third and fourth tubes are on the top of the container. The centrifuge container 39 may also be equipped with a foolproof device 68 constituting a system of identification and which obliges the operator to place it systematically in the same centrifuge bowl 46 on the centrifuge 48. The foolproof device may be in the form of a pin 70 placed in the bottom of the centrifuge bowl 46 that fits into the foolproof device 68 constituted by a cavity made in the bottom of the centrifuge container 39. The information for assigning centrifuge bowl 46 to centrifuge container 39 is recorded on the container's electronic chip 45, so that all information concerning the centrifuge bowl 46 is transferred to the blood bag concerned 40 at the same time as post-centrifuging information is transferred. Then, the operator, using keyboard 38, for example, can enter into the second computerized management device 36, any variable information, such as his identity or incident reports such as double centrifugation should the primary transfused blood bag 40 have been put in its container 45 upside down. When all the information to be possessed by the second computerized management device 36 is available and entered, the centrifuge cycle can be carried out: parameters displayed for the centrifuging operation and real centrifuging characteristics are supplied by the electronic control device 41 and entered directly into the second computerized management device 36, for example the rotation speed in relation to the time can be entered into this device by way of a speed measuring device 47, which, after integrating the data mathematically, enables a centrifugation index to be deduced. After centrifuging, a sixth communication device 42 is used for identifying the primary centrifuged blood bag concerned 40 and the centrifuge container 39 that contains it, so that further information can be entered into it, for example new information concerning centrifuging conditions and notably any information that specifically concerns the centrifuge bowl 46 that held the primary centrifuged blood bag 40. Although, in the description, the electronic communication devices 37, 44, 42 are presented as being different every time, a single electronic communication device can be used for several workstations depending on how it has been programmed. This remark is of course valid for the filtration and separation stations. To improve the operation's reliability, safety devices are put in place that may, for example, prevent the centrifuge from starting up if any information whatsoever has not been collected or transmitted by the second computerised management device 36.

The separation function is composed of a separation device 6 (FIG. 3) equipped with a third computerized management device 43 connected to a seventh electronic communication device 48, to a keyboard 49, and, for example, to an electronic control device 50 that commands the separation cycle. The operator may, for example, enter his identity using keyboard 49 and then, by way of the seventh electronic communication device 48, recopy all the information contained in the primary centrifuged blood bag 40 to store it in the third computerized management device 43. Information coming from the phase separation cycle is incorporated into the third computerized management device 43 and is then transmitted, on the one hand, to the plasma bag 7 containing the plasma phase and, on the other hand, to the primary centrifuged blood bag 40 that now only contains the phase with a high red blood cell content, a part of its contents having come from the anticoagulant bag 8.

A way of transferring this information consists of installing a seventh electronic communication device 48 in the flat door of the first cradle 51 so as to be able to recopy the contents of the chip on the primary centrifuged blood bag 40, only when it is in place for the separation operation; similarly, the eighth and ninth electronic communication devices 52 and 53, connected to the third computerised management device 43, are placed respectively in the doors of the second and third cradles 54 and 55.

The plugs are removed from the fourth, fifth and sixth tubes 56, 66, 63 which are then inserted into a second and third heat-sealing and cutting device 60 and 61 which are also capable of compressing the tube to stop it.

An optical detection device 62 is put on the fourth tube 56. The fourth tube is left open and the sixth tube 63 is compressed closed by the third heat-sealing and cutting device 61.

To begin with, the mobile sidewall 59 in the first cradle 51 ejects the plasma which is pumped into the plasma bag 7 through the second filtration unit 67 on the fifth tube 66, which pushes the mobile sidewall 64 in the second cradle backwards; when the optical detection device 62 detects the arrival of the phase with the high red blood cell content, the mobile sidewall 59 is prevented from moving any further backwards and the plasma bag 7 is then re-closed and separated from the primary centrifuged blood bag 40 by the second heat-sealing and cutting device 60; the third computerised management device 43 sends information to the first electronic chip 57; then the third heat-sealing and cutting device 61 opens up the sixth tube 63 and the mobile sidewall 65 in the third cradle 55 begins to push the anticoagulant into the primary centrifuged blood bag 40, pushing the mobile sidewall 59 in the first cradle 51 backwards, until it reaches its rearmost limit; the third heat-sealing and cutting device 61 closes the sixth tube 63 and separates the anticoagulant bag 8 from the primary centrifuged blood bag 40, which contains the phase with a high red blood cell content; the second electronic chip 58 on the anticoagulant bag 8 is then interrogated by the ninth electronic communication device 53 just before the heat-sealing and cutting process and the information is transferred to the primary electronic chip 33. As the cycle is now finished, the plasma bag 7 and the primary centrifuged blood bag 40 containing the phase with a high red blood cell content can be removed from their cradles 54 and 51. The machine cycle is stopped at each phase for transferring information until all the information awaited or transmitted by the third computerised management device 43 is entered.

In the context of perfecting the invention, the primary electronic chip 33, and the first and second electronic chips 57 and 58 are identified depending on the bags concerned 3, 7, 8, and are then inhibited, with all the uninhibit codes being on the mother blood bag 2. In this way, electronic chips 33, 57, 58, respectively on primary blood bag 3 (successively becoming primary blood bag 30 when it has been filtered and primary centrifuged blood bag 40), plasma bag 7 and anticoagulant bag 8 are un-inhibited one after the other as operations progress by transmitting codes from one point to the next: this mode of operation avoids, for example, sending information intended for the primary blood bag 3, 30, 40 to one of the plasma or anticoagulant bags 7 or 8 by mistake.

The invention claimed is:

1. A method for enhancing reliability of traceability of blood samples resulting from collection of whole blood in a mother blood bag utilizing a system that comprises at least one filtration unit, a centrifuge, electronic control devices, computerized systems, and sampling kits comprising bags connected to each other by tubes, each bag including an electronic chip capable of memorizing and exchanging information with an electronic communication device via a loop antenna, the method comprising:
    producing by separation plasma and a phase with the high red blood cell content using three cradles each equipped with a door and a mobile sidewall that moves with respect to a respective cradle; and
    collecting and processing information, using the computerized systems, from the bags, from processing the bags, and from operators using the system.

2. The method of claim 1, wherein the bags comprise a phase containing platelets.

3. The method of claim 1, wherein contents of the sampling kits vary depending at least on blood products needed.

4. The method of claim 1, wherein the electronic communication devices are structured and arranged to collect and transfer information.

5. The method of claim 1, wherein the centrifuge comprises a centrifuge bowl, a centrifuge container, three cradles each equipped with a door and a mobile sidewall, and wherein the method further comprises separating the plasma and the phase with the high red blood cell content using the three cradles.

6. The method of claim 1, further comprising hanging up the mother blood bag connected to a primary blood bag by a tube.

7. The method of claim 6, before the hanging, reading contents of a mother chip arranged on the mother blood bag using a first electronic communication device and recording the contents on one of the computerized systems.

8. The method of claim 1, further comprising performing filtration and, during the filtration, collecting information from one of the electronic control devices and from the operators and re-transmitting the collected information.

9. The method of claim 8, wherein the collected information is re-transmitting after the mother blood bag has been emptied to a primary electronic chip on a primary blood bag.

10. The method of claim 9, further comprising separating the primary blood bag from the empty mother blood bag and the filtration unit using a heat-sealing and cutting device.

11. A method for enhancing reliability of traceability of blood samples resulting from collection of whole blood in a mother blood bag utilizing a system that comprises at least one filtration unit, a centrifuge, electronic control devices, computerized systems, and sampling kits comprising bags connected to each other by tubes, each bag including an electronic chip capable of memorizing and exchanging information with an electronic communication device via a loop antenna, the method comprising:

producing by separation plasma and a phase with the high red blood cell content using three cradles each equipped with a door and a mobile sidewall that moves with respect to a respective cradle;

collecting and processing information, using the computerized systems, from the bags, from processing the bags, and from operators using the system;

hooking a fixed or mobile hook having a closing device to the mother blood bag;

opening the closing device when said hook is at a hooking-up station and is ready for the mother blood bag to be hooked on for filtering;

closing the closing device during a filtration phase; and re-opening the closing device when said hook arrives at an unloading station.

12. The method of claim 11, further comprising:

unhooking an empty mother blood bag;

re-closing the closing device whilst awaiting a new allocation after information has been transmitted to a primary electronic chip.

13. The method of claim 11, further comprising using a first electromechanical device during opening and placing a helix spring under tension.

14. The method of claim 13, further comprising releasing the tension of the helix spring during a hooking on of the mother blood bag, whereby said hook closes itself by moving downward under pressure of a coil spring.

15. The method of claim 13, further comprising:

opening the closing device at the unloading station using a second electromechanical device, whereby the helix spring is placed under tension;

re-closing the closing device by releasing the tension on the helix spring at the unloading station.

16. The method of claim 1, wherein the system comprises a heat-sealing and cutting apparatus that comprises a first heat-sealing and cutting device that seals a tube via a welding process and cuts the tube in a center of a weld, a first compartment in which an empty mother blood bag is placed, and a second compartment in which a primary blood bag is placed, and wherein the method comprises:

activating with one of the electronic control devices the heat-sealing and cutting apparatus only when all information has been transmitted correctly.

17. The method of claim 1, further comprising:

prior to performing centrifugation of a primary blood bag, transferring information contained in a primary electronic chip to one of the computerized systems; and after the centrifugation, re-transferring information in addition to the transferred information to the primary electronic chip on the primary centrifuged blood bag.

18. A method for enhancing reliability of traceability of blood samples resulting from collection of whole blood in a mother blood bag utilizing a system that comprises at least one filtration unit, a centrifuge, electronic control devices, computerized systems, and sampling kits comprising bags connected to each other by tubes, each bag including an electronic chip capable of memorizing and exchanging information with an electronic communication device via a loop antenna, the method comprising:

producing by separation plasma and a phase with the high red blood cell content using three cradles each equipped with a door and a mobile sidewall that moves with respect to a respective cradle; and collecting and processing information, using the computerized systems, from the bags, from processing the bags, and from operators using the system, wherein the centrifuge comprises a centrifuge container and an electronic container chip possessing information on identification criteria specific to the centrifuge container, whereby the electronic container chip enables information concerning a centrifuge bowl and the centrifuge container to be assigned to a primary centrifuged blood bag.

19. A method for enhancing reliability of traceability of blood samples resulting from collection of whole blood in a mother blood bag utilizing a system that comprises at least one filtration unit, a centrifuge, electronic control devices, computerized systems, and sampling kits comprising bags connected to each other by tubes, each bag including an electronic chip capable of memorizing and exchanging information with an electronic communication device via a loop antenna, the method comprising:

producing by separation plasma and a phase with the high red blood cell content using three cradles each equipped with a door and a mobile sidewall that moves with respect to a respective cradle; and collecting and processing information, using the computerized systems, from the bags, from processing the bags, and from operators using the system, wherein the centrifuge comprises a centrifuge container and a foolproof device, whereby the foolproof device enables information concerning a centrifuge bowl and the centrifuge container to be assigned to a primary centrifuged blood bag.

20. The method of claim 1, wherein the electronic communication devices comprises nine electronic communication devices.

21. The method of claim 1, wherein the bags comprise a primary blood bag, a plasma bag, and an anticoagulant bag.

22. The method of claim 21, wherein one of the computerized systems is structured and arranged to receive all information contained in a primary electronic chip on the primary centrifuged blood bag, wherein another of the computerized systems is structured and arranged to receive information resulting from a anticoagulant bag.

23. The method of claim 1, wherein the electronic communication device comprises a plurality of electronic communication devices.

24. The method of claim 1, wherein the electronic communication device comprises a single electronic communication device.

25. A method for enhancing reliability of traceability of blood samples resulting from collection of whole blood in a mother blood bag utilizing a system that comprises at least one filtration unit, a centrifuge, electronic control devices, computerized systems, and sampling kits comprising bags connected to each other by tubes, each bag including an electronic chip capable of memorizing and exchanging information with an electronic communication device via a loop antenna, the method comprising:
  producing by separation plasma and a phase with the high red blood cell content using three cradles each equipped with a door and a mobile sidewall that moves with respect to a respective cradle; and
  collecting and processing information, using the computerized systems, from the bags, from processing the bags, and from operators using the system,
  wherein the bags comprise a primary blood bag associated with an electronic chip, a plasma bag associated with an electronic chip, and an anticoagulant bag associated with an electronic chip, and wherein the mother blood bag is structured and arranged to contain codes, whereby the electronic chips of the primary blood bag, the plasma bag, and the anticoagulant bag utilize transmitting codes from one point to the next by way of the electronic communication device.

26. A method for enhancing reliability of traceability of a blood sample resulting from collection of whole blood in a mother blood bag utilizing a system that comprises at least one filtration unit, a centrifuge, electronic control devices, and an electronic communication device, the method comprising:
  separating a blood sample into plasma and a phase with the high red blood cell content using cradles each equipped with a door and a mobile sidewall that moves with respect to a respective cradle; and
  collecting and processing information from bags, from processing the bags, and from operators using the system,
  wherein the bags are connected to each other via tubes and each bag includes an electronic chip capable of memorizing and exchanging information with the electronic communication device.

27. A method for enhancing reliability of traceability of a blood sample, the method comprising:
  collecting whole blood in a mother blood bag utilizing a system that comprises at least one filtration unit, a centrifuge, electronic control devices, and an electronic communication device;
  separating a blood sample into plasma and a phase with the high red blood cell content using cradles each equipped with a door and a mobile sidewall; and
  collecting and processing information from bags, from processing the bags, and from operators using the system,
  wherein each bag includes an electronic chip capable of memorizing and exchanging information with the electronic communication device, and
  wherein one of the mobile sidewalls of one of the cradles is structured and arranged to eject plasma and cause an other of the mobile sidewalls on an other of the cradles to move backwards.

* * * * *